US012423464B2

(12) United States Patent
Ricketts et al.

(10) Patent No.: US 12,423,464 B2
(45) Date of Patent: Sep. 23, 2025

(54) SYSTEMS AND METHODS FOR ENCODED CLINICAL DATA COMMUNICATION

(71) Applicant: Hanger, Inc, Austin, TX (US)

(72) Inventors: Antony F. W. Ricketts, Reno, NV (US); Barry A. Thomson, Reno, NV (US); Zlatko L. Hodin, Reno, NV (US)

(73) Assignee: Hanger, Inc., Austin, TX (US)

( * ) Notice: Subject to any disclaimer, the term of this patent is extended or adjusted under 35 U.S.C. 154(b) by 62 days.

(21) Appl. No.: 17/543,887

(22) Filed: Dec. 7, 2021

(65) Prior Publication Data

US 2022/0188453 A1 Jun. 16, 2022

Related U.S. Application Data

(60) Provisional application No. 63/124,227, filed on Dec. 11, 2020.

(51) Int. Cl.
| | | |
|---|---|---|
| *G06F 21/00* | (2013.01) | |
| *G06F 21/36* | (2013.01) | |
| *G06F 21/60* | (2013.01) | |
| *G06F 21/62* | (2013.01) | |
| *G06K 7/14* | (2006.01) | |
| *G16H 10/60* | (2018.01) | |
| *G16H 80/00* | (2018.01) | |

(52) U.S. Cl.
CPC .......... *G06F 21/6245* (2013.01); *G06F 21/36* (2013.01); *G06F 21/606* (2013.01); *G06K 7/1417* (2013.01); *G16H 10/60* (2018.01); *G16H 80/00* (2018.01)

(58) Field of Classification Search
CPC .... G06F 21/6245; G06F 21/36; G06F 21/606; G06F 21/6218; G06F 16/9554; G16H 10/60; G16H 80/00; G16H 40/67; G06K 7/1417; H04W 4/38
See application file for complete search history.

(56) References Cited

U.S. PATENT DOCUMENTS 7,520,419 B2    4/2009  Libin et al.
2012/0226768 A1*  9/2012  Gaines ............... G16H 40/67
                                                         709/217

(Continued)

FOREIGN PATENT DOCUMENTS

EP        2 923 283 B1      5/2020
KR     1020180022764        3/2018

OTHER PUBLICATIONS

International Search Report and Written Opinion on Int'l. Appl. No. PCT/US2021/062103, Dtd Apr. 5, 2022, 11 pps.

*Primary Examiner* — Yogesh Paliwal
(74) *Attorney, Agent, or Firm* — Foley & Lardner LLP

(57) ABSTRACT

A clinical communication system includes a first device, which can include one or more processors configured to receive a first command to receive clinical data from a second device, operate, responsive to receiving the first command, an image capture device, detect, by the image capture device, a first image representing the clinical data, identify a first patient associated with the clinical data, transmit, using communications circuitry, an identifier of the first patient and at least one of the first image or the clinical data to a third device, receive, using the communications circuitry, presentation data corresponding to the clinical data, and present a user interface representing the presentation data.

19 Claims, 7 Drawing Sheets

(56) References Cited

U.S. PATENT DOCUMENTS

| | | | |
|---|---|---|---|
| 2013/0056535 A1* | 3/2013 | Rowlandson | G16H 40/63 235/380 |
| 2013/0197941 A1* | 8/2013 | Cochran | G16H 10/60 705/2 |
| 2014/0152466 A1* | 6/2014 | Wiesner | G16H 40/67 340/870.07 |
| 2015/0066538 A1* | 3/2015 | Dantsker | G16H 40/63 705/2 |
| 2015/0213203 A1* | 7/2015 | Cumbie | G16H 10/65 705/3 |
| 2015/0302159 A1* | 10/2015 | Casse | H04L 67/12 705/2 |
| 2015/0310474 A1* | 10/2015 | Setchell | G06K 7/1404 235/462.25 |
| 2016/0275249 A1* | 9/2016 | Lee | G16H 10/65 |
| 2016/0335400 A1* | 11/2016 | Grant | G16H 10/60 |
| 2017/0270249 A1* | 9/2017 | Beerling | H04W 12/06 |
| 2018/0218782 A1* | 8/2018 | Spotts | H04L 9/0637 |
| 2019/0126039 A1* | 5/2019 | Yoo | A61N 1/36007 |
| 2019/0320898 A1 | 10/2019 | Dirghangi et al. | |
| 2019/0326018 A1* | 10/2019 | Ricketts | G16H 50/20 |

\* cited by examiner

SYSTEMS AND METHODS FOR ENCODED CLINICAL DATA COMMUNICATION

BACKGROUND

The present application claims the benefit of priority to U.S. Provisional Application No. 63/124,227, filed Dec. 11, 2020, the disclosure of which is incorporated herein by reference in its entirety.

BACKGROUND

The present application relates generally to the field of clinical data systems, and more particular to systems and methods for encoded clinical data communication.

Clinical procedures can be performed in which patients undergo various tests according to the procedures. Clinical data regarding the patients can be detected by sensor devices to be provided to a server that maintains a database for the clinical data, such as an electronic medical record database.

SUMMARY

At least one aspect relates to a method for securely transmitting clinical data. The method can include receiving, by one or more first processors of a first device, a first command to receive clinical data from a second device, operating, by the one or more first processors responsive to receiving the first command, an image capture device of the first device responsive to receiving the first command, detecting, by the image capture device, a first image representing the clinical data, identifying, by the one or more first processors, a first patient associated with the clinical data, transmitting, by communications circuitry of the first device, an identifier of the first patient and at least one of the first image or the clinical data to a third device, receiving, by the communications circuitry from the third device, presentation data corresponding to the clinical data, and presenting, by the first device, a user interface representing the presentation data.

At least one aspect relates to a system. The system can include a first device, which can include one or more processors configured to receive a first command to receive clinical data from a second device, operate, responsive to receiving the first command, an image capture device, detect, by the image capture device, a first image representing the clinical data, identify a first patient associated with the clinical data, transmit, using communications circuitry, an identifier of the first patient and at least one of the first image or the clinical data to a third device, receive, using the communications circuitry, presentation data corresponding to the clinical data, and present a user interface representing the presentation data.

At least one aspect relates to a clinical communication system. The clinical communication system can include at least one of a sensor device or a treatment device, a server device, and a portable electronic device. The at least one of the sensor device or the treatment device can be configured to present a first machine readable image representing clinical data while the at least one of the sensor device or the treatment device is at least one of not connected with a cellular data network, is not connected with a WiFi data network, does not have a cellular data transmitter, or does not have a WiFi data transmitter. The portable electronic device can include one or more processors that are configured to detect, using an image capture device, the first machine readable image responsive to receiving a command to receive the first machine readable image, identify a first patient associated with the clinical data, and transmit, using a wireless communications link with a server device, an identifier of the first patient and at least one of the first machine readable image or the clinical data. The server device can be configured to decode the data structure to extract the clinical data, update a patient data record corresponding to the patient in a clinical database maintained by the server device, generate presentation data using the extracted clinical data, and provide the presentation data to the portable electronic device for presentation by the portable electronic device.

These and other aspects and implementations are discussed in detail below. The foregoing information and the following detailed description include illustrative examples of various aspects and implementations, and provide an overview or framework for understanding the nature and character of the claimed aspects and implementations. The drawings provide illustration and a further understanding of the various aspects and implementations, and are incorporated in and constitute a part of this specification.

BRIEF DESCRIPTION OF THE DRAWINGS

The accompanying drawings are not intended to be drawn to scale. Like reference numbers and designations in the various drawings indicate like elements. For purposes of clarity, not every component can be labeled in every drawing. In the drawings:

FIG. 3 is a schematic diagram of an example of a dashboard of an application operated by a clinical communication system.

FIG. 7 is a schematic diagram of an example of presentation of clinical data using the application of FIG. 3.

DETAILED DESCRIPTION

Clinical communication systems can be used to maintain clinical data in electronic medical records (e.g., electronic health records) regarding patients. The clinical data can be detected or received by sensor devices or user input devices. For example, a procedure may be performed in which a patient is requested to perform an action, such as a movement. An electronic device can be used to monitor and record the action. The device can receive user input indicative of the action, such as user input corresponding to fields of a form associated with the procedure.

The device that detects or receives the clinical data can be unable to or prevented from communication with electronic networks that would otherwise enable transmitting the clinical data to a remote device, such as a server that can process the clinical and that may maintain a clinical database that includes an electronic medical record of the patient. For example, the procedure may be performed in a location in which a wireless communications network, such as a cellular data network or WiFi network, is not present or has insufficient signal strength to allow for transmission of the clinical data. The device may not include transmission electronics, such as radios, for wireless communications (e.g., to reduce size, weight, and power requirements of the device), or may have such electronics deactivated while an application that operates with the clinical data is in use manually or programmatically (e.g., while in use the application may execute an interlock that prevents transmissions of the clinical data), such as to protect the privacy of the patient by restricting output of the clinical data.

Systems and methods in accordance with the present disclosure can enable output and further processing of clinical data from such devices even if the devices are not able to transmit the clinical data using communication networks. For example, the device can encode the clinical data into an image that represents the clinical data in a machine readable format, such as a quick response (QR) code. A remote device, such as a portable electronic device, can detect the image and transmit the image or data extracted from the image to the server for further processing, and can receive a processed (e.g., decoded) representation of the clinical data for local presentation, processing, and interaction by a user. This can enable privacy and security of the transmission of the clinical data to be protected, even where direct transmission of the clinical data to the server is not performed.

Figure 1:
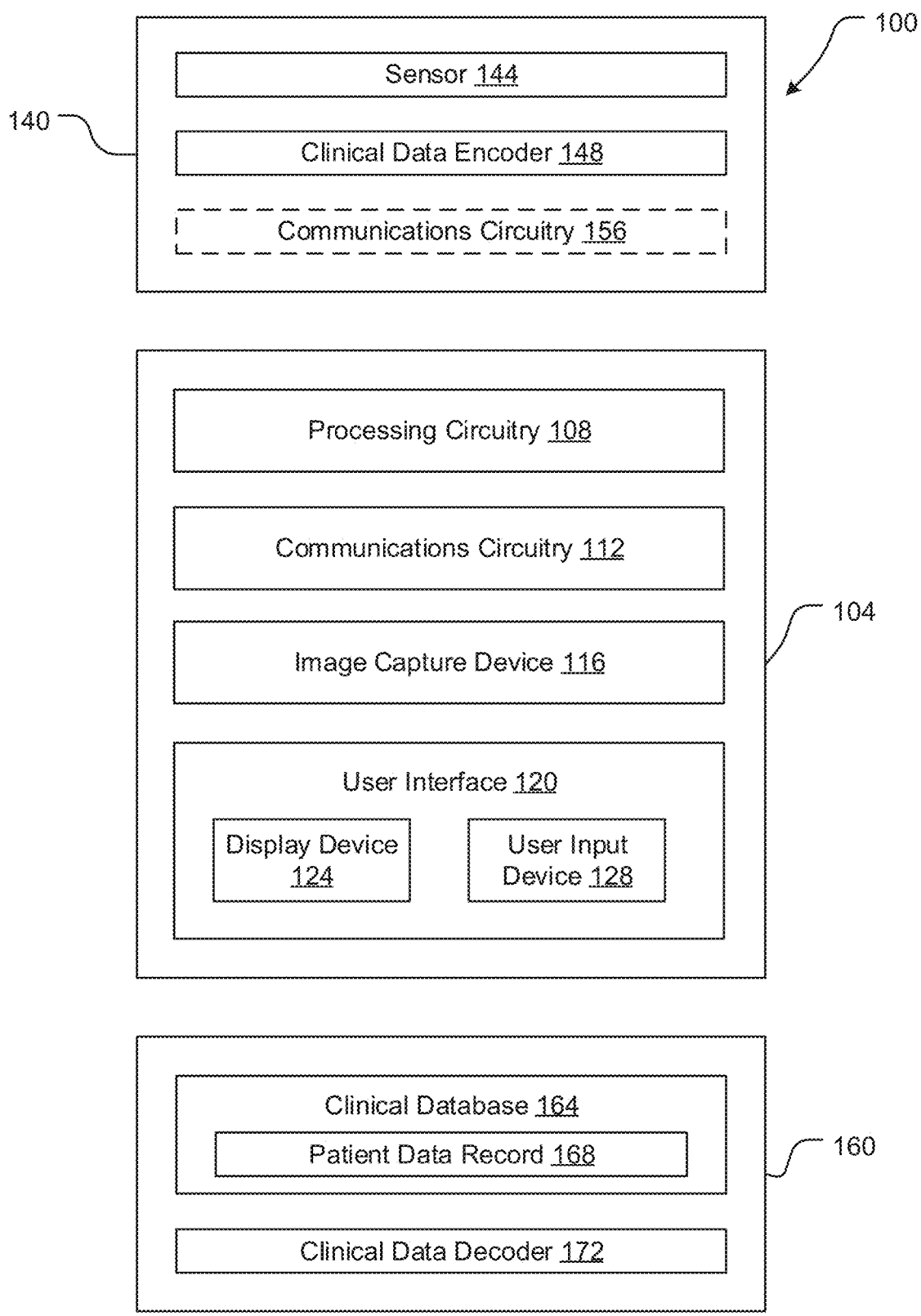
FIG. 1 is a block diagram of an example of a clinical communication system.

FIG. 1 depicts an example of a clinical communication system 100 ("CCS" 100). The clinical communication system 100 can be used to securely receive, store, process, transmit, and present clinical data regarding patients, including in situations where a device that detects or generates the clinical data is not able to establish electronic communications links with other devices.

The CCS 100 can include a first device 104. The first device 104 can be a portable electronic device, such as a cell phone or tablet device. The first device 104 can include processing circuitry 108. The processing circuitry 108 can include one or more processors and memory. The processor may be implemented as a specific purpose processor, an application specific integrated circuit (ASIC), one or more field programmable gate arrays (FPGAs), a group of processing components, or other suitable electronic processing components. The memory is one or more devices (e.g., RAM, ROM, flash memory, hard disk storage) for storing data and computer code for completing and facilitating the various user or client processes, layers, and modules described in the present disclosure. The memory may be or include volatile memory or non-volatile memory and may include database components, object code components, script components, or any other type of information structure for supporting the various activities and information structures of the inventive concepts disclosed herein. The memory is communicably connected to the processor and includes computer code or instruction modules for executing one or more processes described herein. The memory includes various circuits, software engines, and/or modules that cause the processor to execute the systems and methods described herein. In some embodiments, the processing circuitry 108 executes an application ("app"), which may be specifically configured for execution on the first device 104. The processing circuitry 108 may be configured to communicate with a remote application storage server (e.g., application store) to receive updates for the application automatically and/or in response to user input indicating instructions to update the application.

The first device 104 can include communications circuitry 112. The communications circuitry 112 can receive and transmit electronic data transmissions. The communications circuitry 112 can include wired or wireless communication receivers/transmitters (e.g., a USB port, an Ethernet port, a wireless transceiver, etc.). The communications circuitry 112 can include wired or wireless communications interfaces (e.g., jacks, antennas, transmitters, receivers, transceivers, wire terminals, etc.) for conducting data communications external systems or devices. The communications can be direct (e.g., local wired or wireless communications) or via a communications network (e.g., a WAN, the Internet, a cellular network, etc.). For example, the communications circuitry 112 can include a USB port or an Ethernet card and port for sending and receiving data via an Ethernet-based communications link or network. The communications circuitry 112 can include a Wi-Fi transceiver for communicating via a wireless communications network or cellular or mobile phone communications transceivers.

The first device 104 can include an image capture device 116. The image capture device 116 can be a camera, including a video camera. The image capture device 116 can include visible light cameras (e.g., color or black and white), infrared cameras, ultraviolet sensors, or combinations thereof.

The first device 104 can include a user interface 120. The user interface 120 can include a display device 124 and a user input device 128. In some embodiments, the display device 124 and user input device 128 are each components of an integral device (e.g., touchpad, touchscreen, device implementing capacitive touch or other touch inputs). The user input device 128 may include one or more buttons, dials, sliders, keys, or other input devices configured to receive input from a user. The display device 124 may include one or more display devices (e.g., LEDs, LCD displays, etc.). The user interface 120 may also include output devices such as speakers, tactile feedback devices, or other output devices configured to provide information to a user. In some embodiments, the user input device 128 includes a microphone, and the processing circuit 104 includes a voice recognition engine configured to execute voice recognition on audio signals received via the microphone, such as for extracting commands from the audio signals.

Figure 3:
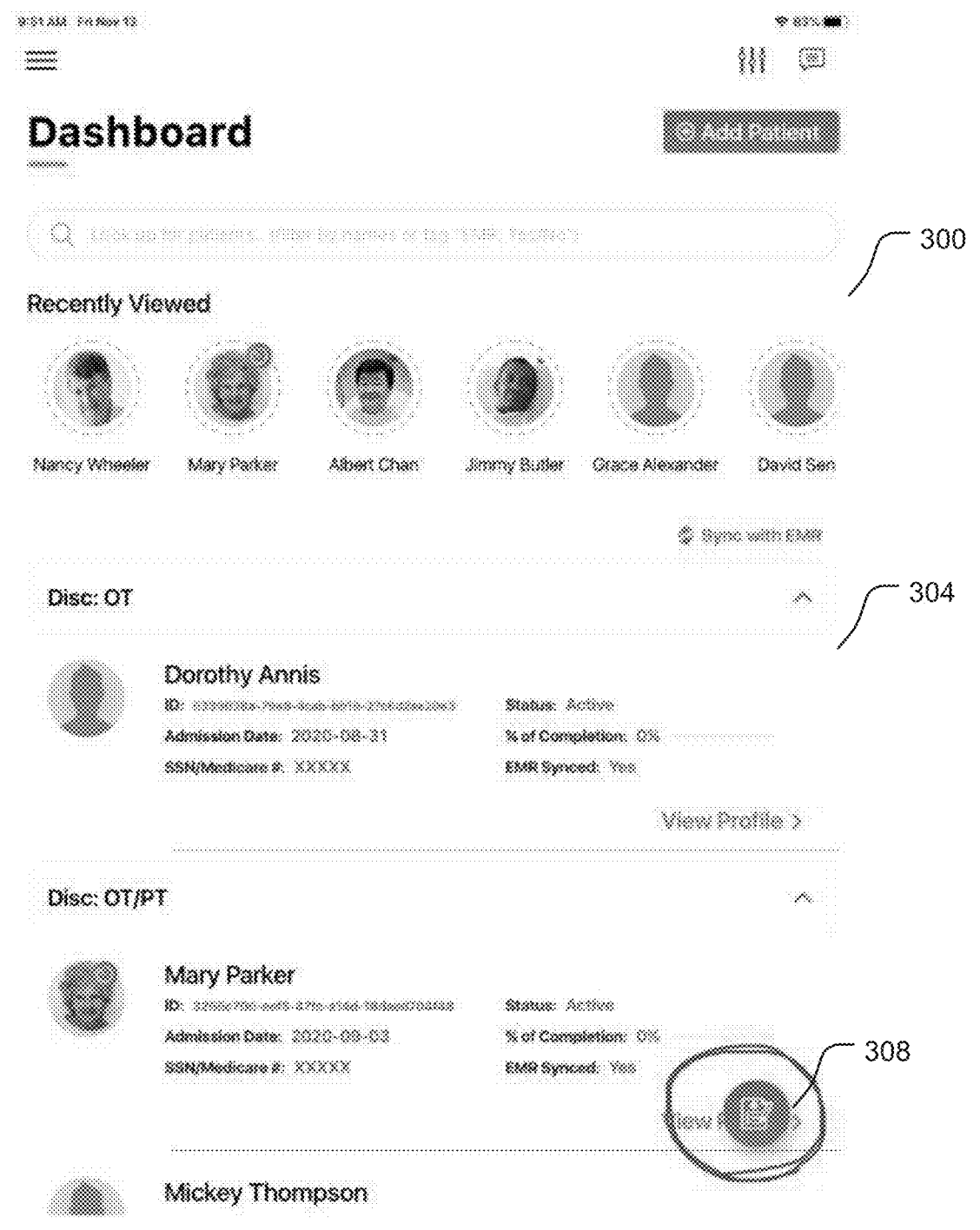

The processing circuitry 104 can execute an application associated with receiving, storing, and transmitting the clinical data. For example, as depicted in FIG. 3, the processing circuitry 104 can execute an application 300 that presents a user interface 304 that includes information regarding at least one patient, including information regarding procedures performed or to be performed for the patient. The user interface 304 can include a connection element 308. Responsive to receiving a command to activate the connection element 308 (e.g., a touch input), the application 300 can initiate a process for detecting an image representative of clinical data.

Referring further to FIG. 1, the CCS 100 can include a second device 140. The second device 140 can incorporate features of the first device 104, such as processing circuitry and user interface components. For example, the second device 140 can be a portable electronic device. The second device 140 can include a sensor 144, such as a camera, position sensor (e.g., at least one of an accelerometer or a gyroscope), temperature sensor, or other sensor that can be used to detect sensor data regarding the patient. The second device 140 can include or be associated with a treatment device, such as an electrotherapy treatment device, and can output clinical data indicating parameters of the treatment (e.g., therapy or therapy session) being performed, such as durations and dosages of treatment and responses of the patient to the treatment.

The second device 140 can receive sensor data and generate the clinical data from the sensor data, such as by generate a clinical data structure that represents the sensor data or portions thereof. The second device 140 can filter the sensor data to extract information to assign to one or more fields of the clinical data structure. The second device 140 can receive the clinical data through the user interface, such as if an operator of the second device 140 is monitoring a procedure, such as a movement, performed by the patient and providing input indicative of the procedure.

The second device 140 can include a clinical data encoder 148. The clinical data encoder 148 can include any function, operation, routine, logic, or instructions executed by processing circuitry of the second device 140 to perform operations such as encoding the clinical data. The clinical data encoder 148 can receive the clinical data (e.g., in a data structure form in which one or more fields of the clinical data structure are assigned data such as name, age, sex, procedure or treatment being performed, information received or detected regarding the patient) and perform an encoding process to generate an image (e.g., encoded image) that is a machine readable representation of the clinical data. For example, the clinical data encoder 148 can generate a QR code from the clinical data. The clinical data encoder 148 can dynamically generate the image, such as to generate a unique image each instance of generating the image, which can improve the security of the data transmission. For example, the clinical data encoder 148 can generate the image dynamically as each instance of generating the image as each instance will incorporate unique clinical data (e.g., varying information received or detected regarding the patient).

The clinical data encoder 148 can perform the encoding process so that the image represents one or more data elements of the clinical data structure. For example, the clinical data encoder 148 can apply a QR code generator or other image encoding process to one or more data elements of the clinical data structure to generate the image, such that features of the image (e.g., values assigned to one or more pixels of the image, such as intensity or color (including black or greyscale) values), are a function of the clinical data structure. For example, the clinical data encoder 148 can use, as input, data elements such as time stamp, patient identifier, session identifier, and therapy session data (how long the therapy was, what protocol was performed, the results of the therapy session) to generate the image.

The clinical data encoder 148 can apply an encryption to the clinical data structure to encrypt the image. For example, the clinical data encoder 148 can encrypt the clinical data structure responsive to a user input indicating instructions to encrypt the clinical data structure. The clinical data encoder 148 can cause the second device 140 to present a user interface requesting the instructions to encrypt the clinical data structure (e.g., from a person performing or managing the therapy) and encrypt the clinical data structure responsive to receiving the user input. The clinical data encoder 148 can use various encryption operations or algorithms to encrypt the image (e.g., to encrypt the data of the clinical data structure in order to generate the image from the encrypted data), such as various symmetric or asymmetric encryption algorithms.

The second device 140 can include a display (which can be part of a user interface). The display can display the image representing the clinical data. The second device 140 can use the display to display the image responsive to receiving a command to display the image. The second device 140 can initiate a timer responsive to displaying the image, and discontinue displaying the image responsive to the timer exceeding a threshold.

The second device 140 can be configured to be unable to transmit the clinical data or a representation thereof using an electronic (e.g., wired or wireless network) connection. For example, the second device 140 can not include communications circuitry, such as a cellular or WiFi radio transmitter, that could be used to transmit the clinical data, such as if the second device 140 is a relatively lightweight device. In some embodiments, the second device 140 includes communications circuitry 156, which may include electronics for transmitting data from the second device 140. The clinical data encoder 148 can be configured to prevent transmission of the clinical data by the communications circuitry 156. For example, the clinical data encoder 148 can store the clinical data in a portion of memory that is isolated from applications that use the communications circuitry 156. The clinical data encoder 148 can operate an interlock that deactivates the communications circuitry 156 or disconnects the communications circuitry 156 from the clinical data encoder 148 while the clinical data encoder 148 is operating.

Figure 4:
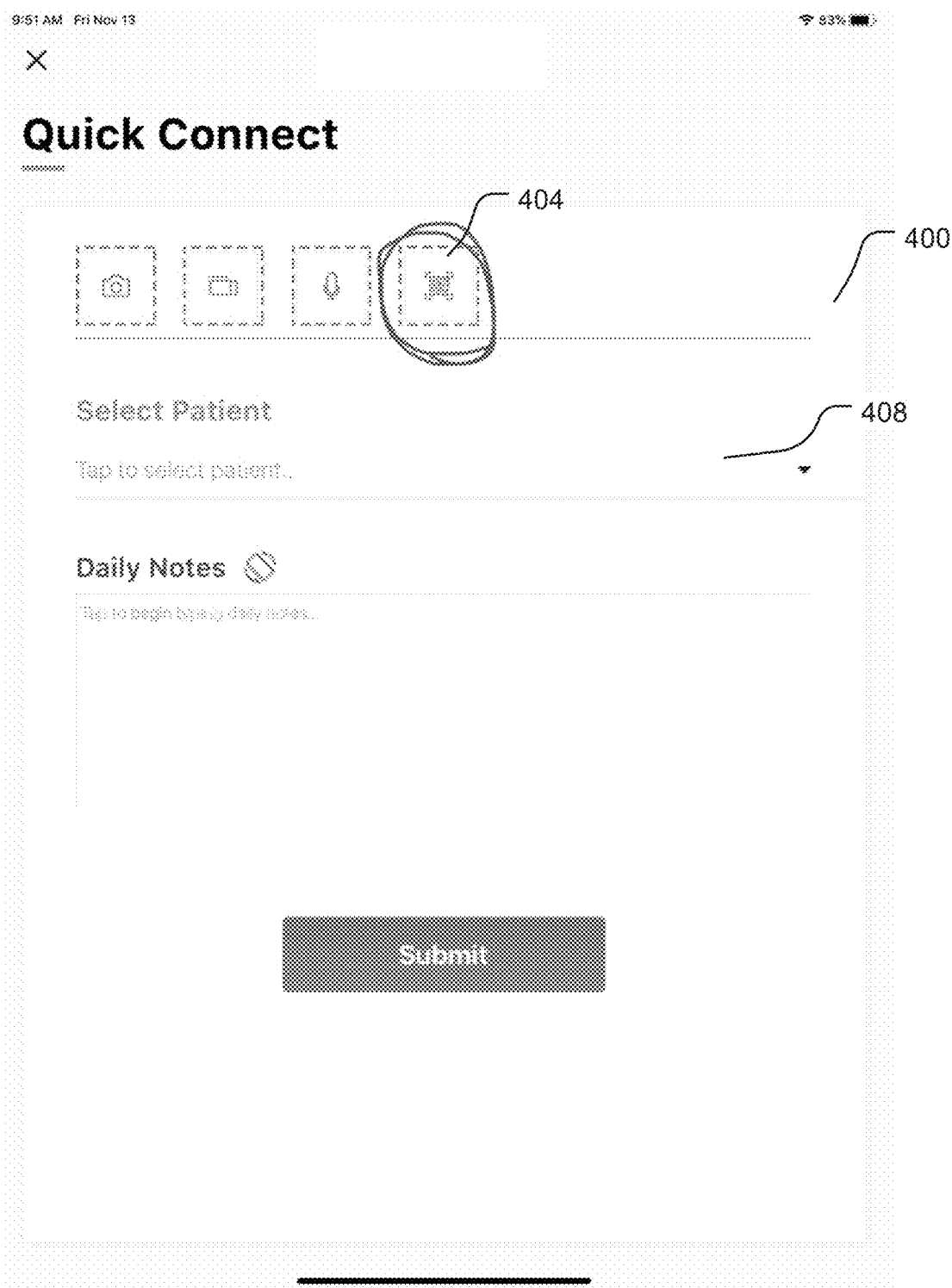
FIG. 4 is a schematic diagram of an example of an image capture element of the application of FIG. 3.
Figure 5:
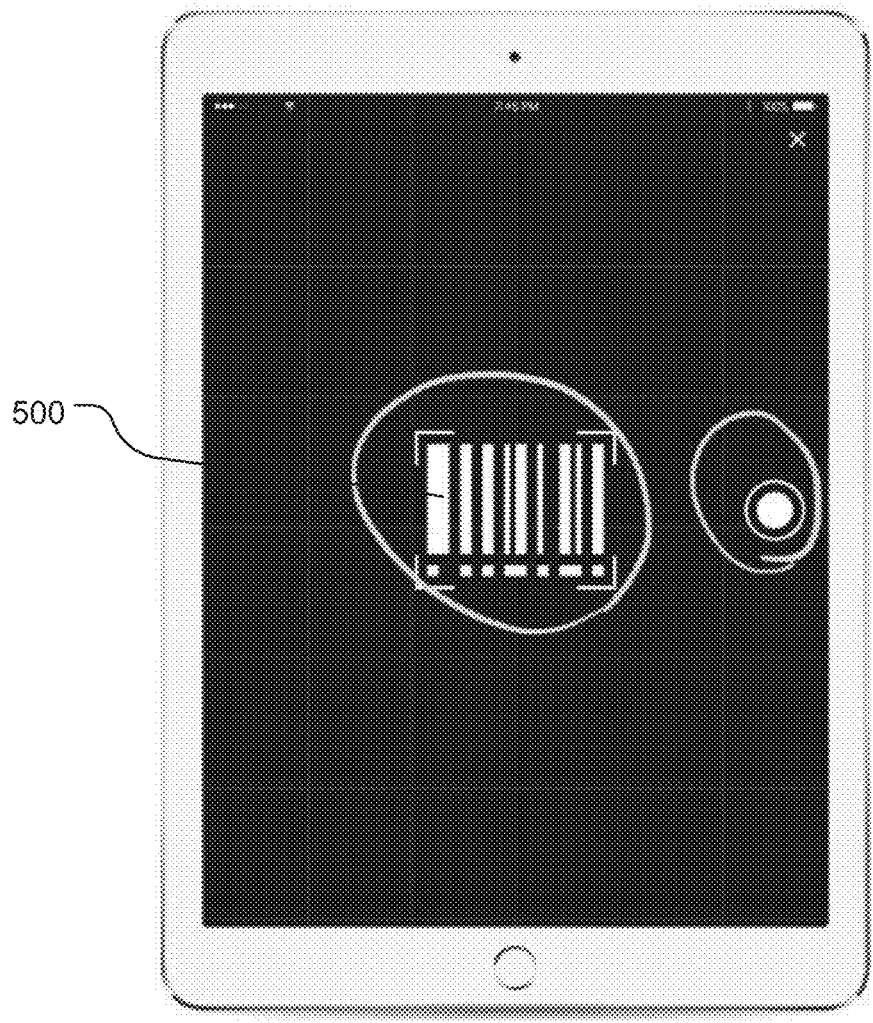
FIG. 5 is an example of an image detection element of the application of FIG. 3.
Figure 6:
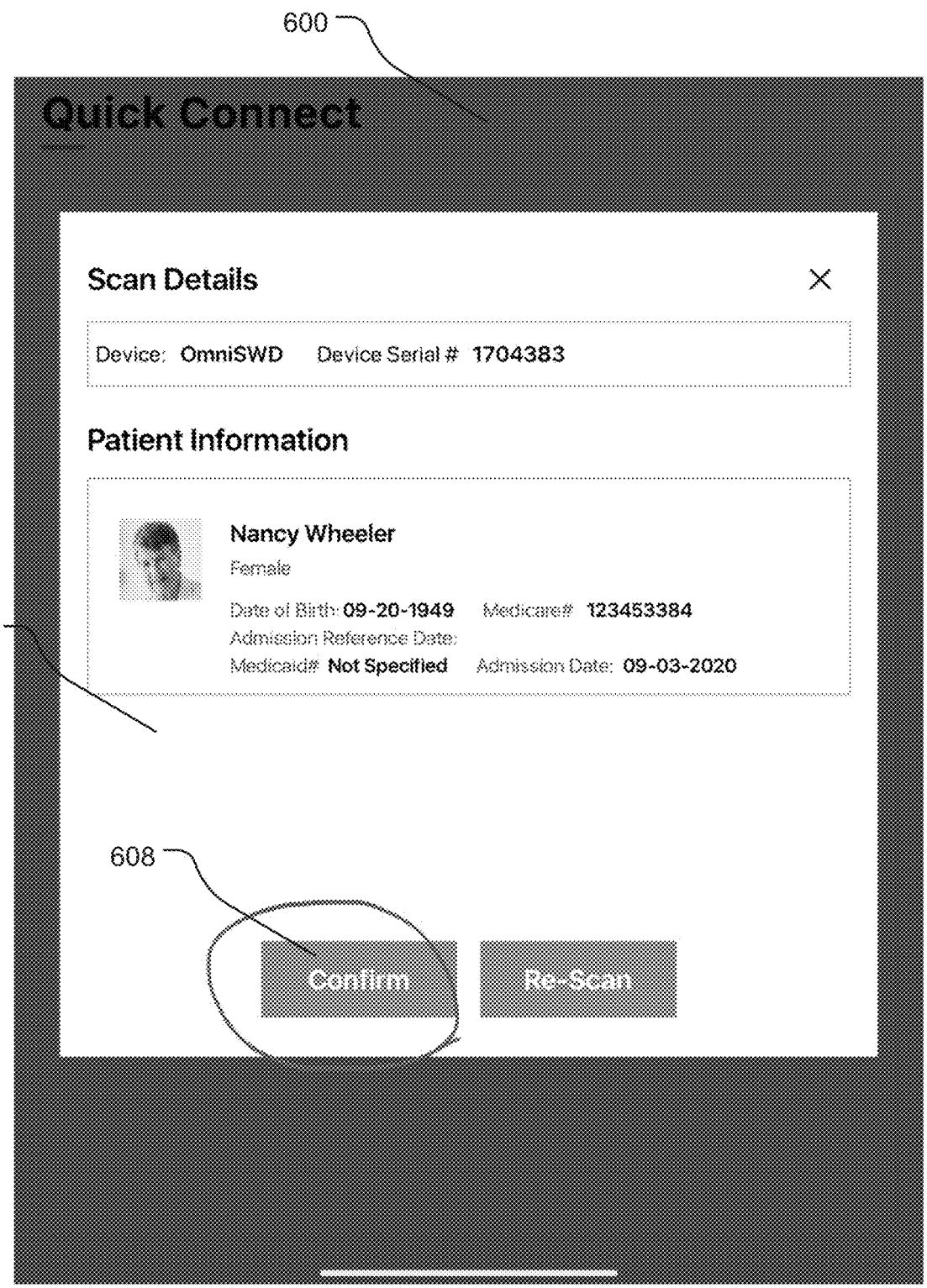
FIG. 6 is a schematic diagram of an example of an interface of the application of FIG. 3.

As depicted in FIG. 4, the application 300 operated by the first device 104 can include a connector 400 that is activated (e.g., launched) responsive to activation of the connection element 308. The connector 400 can include an image capture element 404 that can be activated to cause the image capture device 116 of the first device 104 to activate, enabling the image capture device 116 to detect an image 500 presented by the second device 140 as depicted in FIG. 5 (e.g., responsive to receiving a command to capture the image 500 the image capture device 116). The processing circuitry 104 can use the image capture device 116 to periodically monitor image data from the image capture device 116 to detect the image. The image 504 can be a machine readable representation of the clinical data, such as a QR code. The connector 400 can cause an interface 600 to be populated with data 604 extracted from the machine readable representation, and provide a user interface element 608 to cause re-activation of the connector 400.

The connector 400 can include a patient identifier element 408 (e.g., drop-down menu), which can be used to select an identifier of the patient for which clinical data is to be received.

Referring further to FIG. 1, the processing circuitry 104 can receive the image detected by the image capture device 116. The processing circuitry 104 can identify the patient (e.g., identify an identifier of the patient, such as a name of the patient or an identifier code assigned to the patient). For example, the processing circuitry 104 can use information received via the patient identifier element 408 to identify the patient, or can process at least a portion of the image to extract an identifier of the patient.

The processing circuitry 104 can output the image (e.g., for reception by third device 160) using the communications circuitry 156, enabling remote processing of the clinical data that the image represents even if the second device 140 is prevented from outputting the clinical data. The processing circuitry 104 can output the image together with the identifier of the patient. The processing circuitry 104 can use the communications circuitry 156 to establish a secure wireless connection with the third device 160, such as an encrypted connection. The processing circuitry 104 can output a data structure extracted from the image.

The CCS 100 can include a third device 160. The third device 160 can be remote from the first device 104. The third device 160 can include one or more server devices, such as cloud server devices. The third device 160 can include processing circuitry to perform operations on clinical data. The third device 160 can include or be coupled with communications circuitry to allow the third device 160 to receive and transmit data over a network 180. The network 180 can enable the first device 104 and third device 160 to communicate using the Internet.

The third device 160 can include a clinical database 164. The clinical database 164 can be an electronic medical record system. The clinical database 164 can store and maintain a plurality of patient data records 168 corresponding to respective patients. The patient data record 168 can include an identifier of the patient along with data such as name, age, sex, procedure or treatment being performed, information received or detected regarding the patient.

The third device 160 can include a clinical data decoder 172. The clinical data decoder 172 can receive the image (e.g., a data structure or other machine readable representation of the clinical data received from the first device 104) and decode the image to extract the clinical data, such as to extract a data structure that defines the clinical data. For example, the clinical data decoder 172 can perform a QR decoding process to extract the data structure. The clinical data decoder 172 can use the identifier of the patient to assign the clinical data to the patient data record 168 that corresponds with the patient and the clinical data. The clinical data decoder 172 can decode the clinical data and modify the clinical data (e.g., translate) into information specific to the second device 140 that generated the clinical data, such as to identify information regarding treatments being provided to the patient or particular types of sensor data detected by the second device 140, in order to assign the information to corresponding fields of the patient data record 168. The clinical data decoder 172 can decrypt the image (or the clinical data extracted from the image) responsive to the clinical data being encrypted, such as by using a decryption key associated with the encryption process performed by the clinical data encoder 148.

Figure 7:
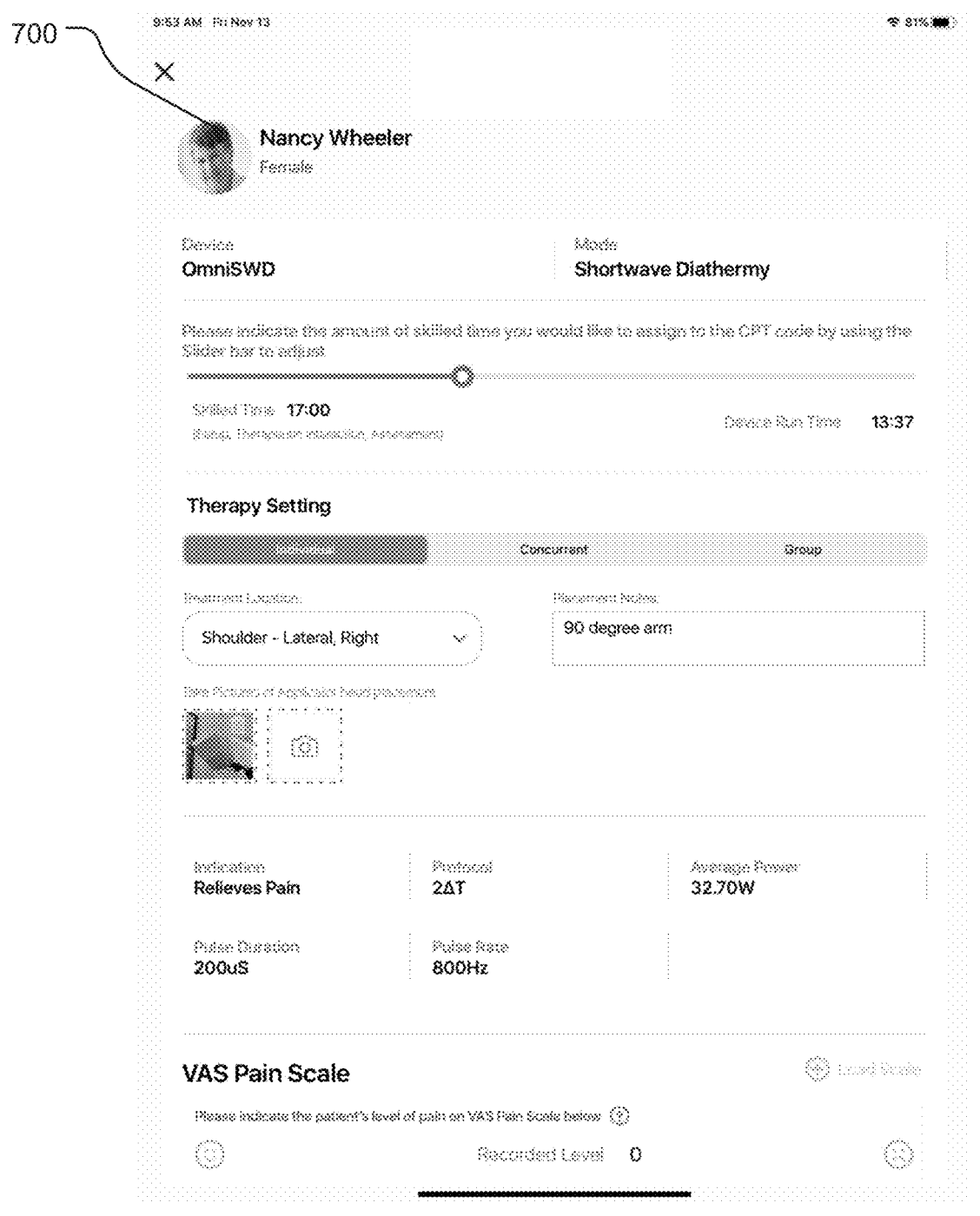

The third device 160, responsive to decoding the image or other machine readable representation of the clinical data, can generate presentation data. The presentation data can correspond to documentation to be presented by the first device 104. For example, as depicted in FIG. 7, the first device 104 can present, using the application 300, presentation data 700 that includes information such as an identifier of the second device 140 and information regarding a treatment performed using the second device 140.

Figure 2:
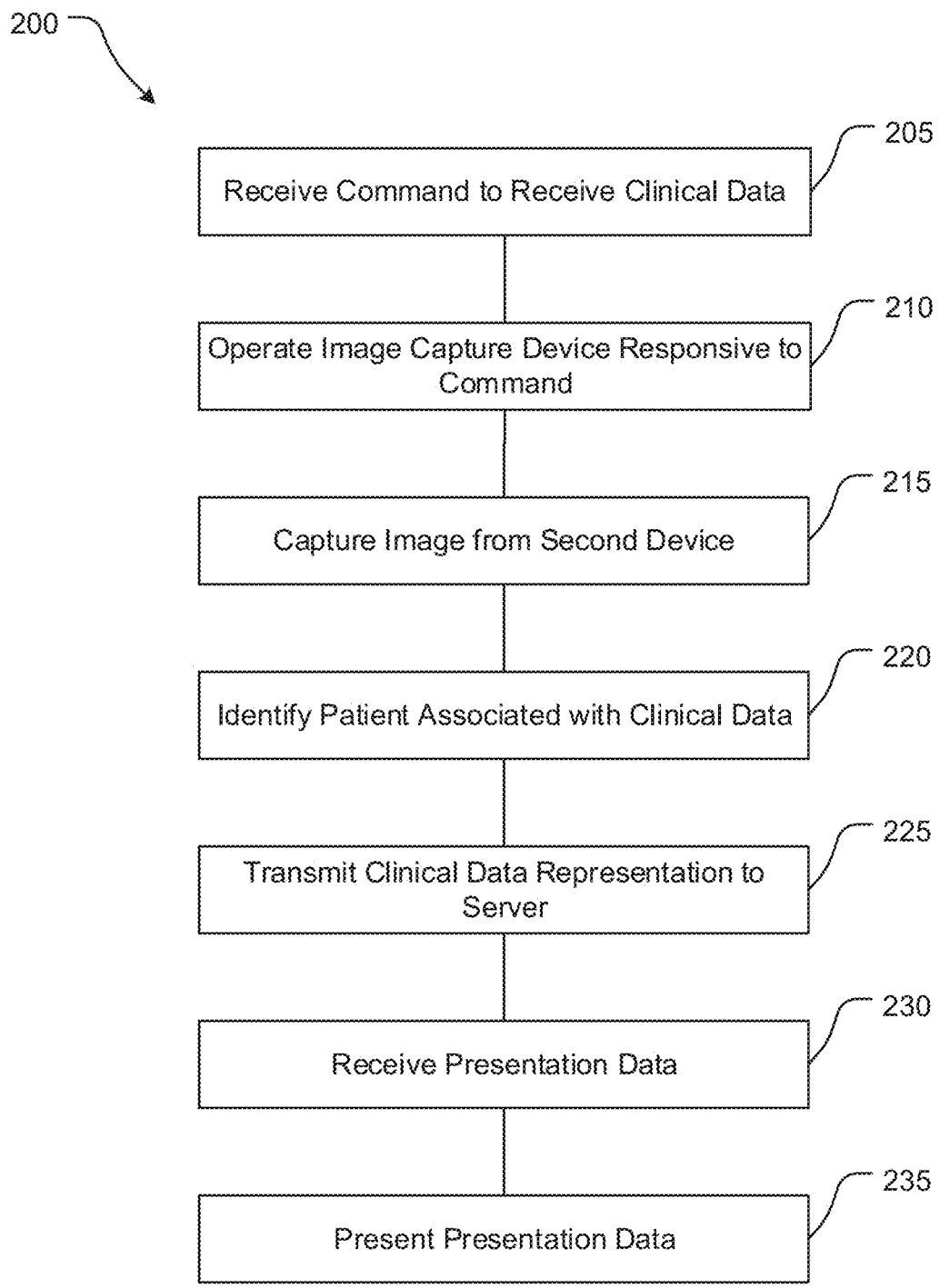
FIG. 2 is a flow diagram of an example of a method for securely transmitting clinical data using a clinical communication system.

FIG. 2 depicts a method 200 for securely transmitting clinical data. The method 200 can be performed using various systems and devices described herein, such as the CCS 100 and components thereof. The method 200 or portions can be performed responsive to commands and other inputs received from a user, such as a medical professional, managing a procedure or treatment for a patient, such as to gather clinical data regarding the patient and securely upload the clinical data to a cloud server that maintains electronic medical record information, which can be processed by the cloud server and provided to a device operated by the user for further updating.

A command can be received by a first device to receive clinical data regarding a patient from a second device (205). The first device can be a client device operated by a user. The first device can be a portable electronic device. The command can be received via a user interface presented by an application executed by the first device. The command can identify the patient. The command can identify the second device, which can be a portable electronic device, a sensor that detects sensor data used to generate the clinical data, or a treatment device that is used to perform a treatment on the patient.

An image capture device of the first device can be operated responsive to the command (210). For example, the application can receive the command and initiate the image capture device responsive to the command, such as to present image data detected by the image capture device using the application.

The image capture device can capture an image responsive to a command (e.g., a user input indicating instructions to capture the image) (215). The first device can periodically monitor image data from the image capture device, and capture the image responsive to detecting one or more expected features of a target image. For example, the second device can generate an image as a machine readable representation of the clinical data. The first device can monitor the image data to identify one or more expected features of the machine readable representation, and capture an image of the machine readable representation responsive to detecting the one or more expected features. The expected features can include a machine readable code identifying the patient or the clinical data.

A patient associated with the clinical data can be identified by the first device (220). The patient can be identified by extracting an identifier of the patient from the image. For example, the first device can search a portion of the image in which the identifier is expected to be encoded to extract the identifier. The first device can identify the patient based on the identifier being provided to the application or selected during use of the application.

At least one of the image or the clinical data can be transmitted by the first device to a third device (225). The first device can establish a secure communications link with the third device to transmit the at least one of the image or the clinical data. The first device can transmit the identifier of the patient to the third device. The third device can be a server, such as a cloud server, that can maintain a clinical database (e.g., electronic medical record database), and update the clinical database using the clinical data. The third device can decode the machine readable representation of the clinical data in order to update the clinical database. The third device can generate presentation data based on the clinical data, such as to generate a presentation data structure in which values of the clinical data are assigned to fields for presentation of the clinical data.

The first device can receive the presentation data (230). For example, the first device can use the secure communications link to receive the presentation data from the third device, such as to receive the presentation data structure in order to present the presentation data.

The first device can present the presentation data (235). For example, the first device can use the application to present the presentation data using the user interface of the first device. The first device can receive input via the user interface to update the clinical data, such as to update the electronic medical record of the patient.

All or part of the processes described herein and their various modifications (hereinafter referred to as "the processes") can be implemented, at least in part, via a computer program product, i.e., a computer program tangibly embodied in one or more tangible, physical hardware storage devices that are computer and/or machine-readable storage devices for execution by, or to control the operation of, data processing apparatus, e.g., a programmable processor, a computer, or multiple computers. A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a network.

Processors suitable for the execution of a computer program include, by way of example, both general and special purpose microprocessors, and any one or more processors of any kind of digital computer. Generally, a processor will receive instructions and data from a read-only storage area or a random access storage area or both. Elements of a computer (including a server) include one or more processors for executing instructions and one or more storage area devices for storing instructions and data. Generally, a computer will also include, or be operatively coupled to receive data from, or transfer data to, or both, one or more machine-readable storage media, such as mass storage devices for storing data, e.g., magnetic, magneto-optical disks, or optical disks.

Computer program products are stored in a tangible form on non-transitory computer readable media and non-transitory physical hardware storage devices that are suitable for embodying computer program instructions and data. These include all forms of non-volatile storage, including by way of example, semiconductor storage area devices, e.g., EPROM, EEPROM, and flash storage area devices; magnetic disks, e.g., internal hard disks or removable disks; magneto-optical disks; and CD-ROM and DVD-ROM disks and volatile computer memory, e.g., RAM such as static and dynamic RAM, as well as erasable memory, e.g., flash memory and other non-transitory devices.

The construction and arrangement of the systems and methods as shown in the various embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced. Other substitutions, modifications, changes, and omissions may be made in the design, operating conditions and arrangement of embodiments without departing from the scope of the present disclosure.

As utilized herein, the terms "approximately," "about," "substantially", and similar terms are intended to include any given ranges or numbers +/−10%. These terms include insubstantial or inconsequential modifications or alterations of the subject matter described and claimed are considered to be within the scope of the disclosure as recited in the appended claims.

It should be noted that the term "exemplary" and variations thereof, as used herein to describe various embodiments, are intended to indicate that such embodiments are possible examples, representations, or illustrations of possible embodiments (and such terms are not intended to connote that such embodiments are necessarily extraordinary or superlative examples).

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

The term "or," as used herein, is used in its inclusive sense (and not in its exclusive sense) so that when used to connect a list of elements, the term "or" means one, some, or all of the elements in the list. Conjunctive language such as the phrase "at least one of X, Y, and Z," unless specifically stated otherwise, is understood to convey that an element may be either X, Y, Z; X and Y; X and Z; Y and Z; or X, Y, and Z (i.e., any combination of X, Y, and Z). Thus, such conjunctive language is not generally intended to imply that certain embodiments require at least one of X, at least one of Y, and at least one of Z to each be present, unless otherwise indicated.

References herein to the positions of elements (e.g., "top," "bottom," "above," "below") are merely used to describe the orientation of various elements in the FIGURES. It should be noted that the orientation of various elements may differ according to other exemplary embodiments, and that such variations are intended to be encompassed by the present disclosure.

The present disclosure contemplates methods, systems and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

Although the figures show a specific order of method steps, the order of the steps may differ from what is depicted.

Also two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

What is claimed is:

1. A method for securely transmitting clinical data, comprising:
   receiving, by one or more first processors of a first device, by an application of the first device, a first command to receive clinical data from a second device, the clinical data corresponding to a plurality of parameters comprising a treatment of electrotherapy performed on a first patient, a duration of the treatment, a dosage of the treatment, and a response of the first patient to the treatment;
   receiving, by the one or more first processors, by the application, a selection of an identifier of the first patient;
   operating, by the one or more first processors responsive to receiving the first command, an image capture device of the first device to detect a first image representing the clinical data by periodically monitoring image data to identify one or more features of the first image, wherein the first image is a quick response (QR) code, the image capture device capturing the image responsive to detecting the one or more identified features of the first image;
   encrypting, by the one or more first processors, the identifier of the first patient and at least one of the first image or the clinical data;
   transmitting, by communications circuitry of the first device, the encrypted identifier of the first patient and at least one of the encrypted first image or the encrypted clinical data to a third device;
   receiving, by the communications circuitry from the third device, presentation data corresponding to the clinical data; and
   presenting, by the first device, a user interface representing the presentation data.

2. The method of claim 1, further comprising:
   detecting, by a sensor of the second device, sensor data regarding the first patient;
   generating, by one or more second processors of the second device, the clinical data using the sensor data; and
   generating, by the one or more second processors, the first image as a machine readable representation of the clinical data.

3. The method of claim 1, wherein the second device is not connected with a cellular data network, is not connected with a WiFi data network, does not have a cellular data transmitter, or does not have a WiFi data transmitter.

4. The method of claim 1, further comprising:
   extracting, by the one or more first processors, a data structure comprising the clinical data from the first image, wherein transmitting the at least one of the first image or the clinical data comprises transmitting the data structure.

5. The method of claim 4, further comprising:
   decoding, by one or more third processors of the third device, the data structure to extract the clinical data;
   updating, by the one or more third processors, a patient data record corresponding to the first patient in a clinical database maintained by the third device; and
   generating, by the one or more third processors, the presentation data using the extracted clinical data.

6. The method of claim 1, wherein identifying the first patient comprises at least one of:
   (i) identifying the first patient from an active session of the application executed by the one or more first processors; or
   (ii) extracting the identifier of the first patient from the clinical data.

7. The method of claim 1, further comprising:
   establishing, by the communications circuitry, a secure wireless connection with the third device, wherein transmitting the identifier of the first patient and the at least one of the first image or the clinical data comprises transmitting the identifier of the first patient and the at least one of the first image or the clinical data using the secure wireless connection.

8. The method of claim 1, wherein the identifier is extracted from at least one portion of the first image.

9. The method of claim 1, wherein presenting, by the first device, the presentation data comprises presenting, by the first device, an identifier of the second device and information regarding the treatment performed using the second device.

10. The method of claim 1, further comprising:
    initiating a timer, by the second device, responsive to displaying the first image, and
    discontinuing display of the first image responsive to the timer expiring.

11. A system, comprising:
    a first device comprising one or more hardware processors configured to:
    receive a first command to receive clinical data from a second device;
    operate, responsive to receiving the first command, an image capture device to detect a first image representing the clinical data by periodically monitoring image data to identify one or more features of the first image, wherein the first image is a quick response (QR) code, wherein the image capture device of the first device captures the first image responsive to detecting the one or more identified features of the first image;
    receive a selection, by a user interface element presented by the first device, of an identifier of a first patient associated with the clinical data;
    encrypt the identifier of the first patient and at least one of the first image or the clinical data;
    transmit, using communications circuitry, the identifier of the first patient and at least one of the first image or the clinical data to a third device;
    receive, using the communications circuitry, presentation data corresponding to the clinical data; and
    present a user interface representing the presentation data.

12. The system of claim 11, wherein the second device comprises:
    at least one sensor configured to detect sensor data regarding the first patient; and
    one or more second hardware processors configured to generate the clinical data using the sensor data and generate the first image as a machine readable representation of the clinical data.

13. The system of claim 11, wherein the one or more processors are configured to extract a data structure comprising the clinical data from the first image, wherein the communications circuitry is configured to transmit the at least one of the first image or the clinical data by transmitting the data structure.

14. The system of claim 13, wherein the third device comprises one or more processors configured to:
- decode the data structure to extract the clinical data;
- update a patient data record corresponding to the first patient in a clinical database maintained by the third device; and
- generate the presentation data using the extracted clinical data.

15. The system of claim 11, wherein the image capture device is configured to detect the first image responsive to receiving a second command to detect the first image.

16. The system of claim 11, wherein the one or more first processors are configured to identify the first patient by at least one of:
- (i) identifying the first patient from an active session of an application executed by the one or more processors; or
- (ii) extracting the identifier of the first patient from the clinical data.

17. The system of claim 11, wherein the communications circuitry is configured to:
- establish a secure wireless connection with the third device and transmit the identifier of the first patient and the at least one of the first image or the clinical data comprises transmitting the identifier of the first patient and the at least one of the first image or the clinical data using the secure wireless connection.

18. A clinical communication system, comprising:
- at least one of a sensor device configured to detect clinical data regarding a patient or a treatment device configured to apply a treatment to the patient associated with clinical data, the clinical data corresponding to a plurality of parameters comprising a treatment of electrotherapy performed on a first patient, a duration of the treatment, a dosage of the treatment, and a response of the first patient to the treatment, the at least one of the sensor device or the treatment device configured to present a first machine readable image representing the clinical data while the at least one of the sensor device or the treatment device is at least one of not connected with a cellular data network, is not connected with a WiFi data network, does not have a cellular data transmitter, or does not have a WiFi data transmitter;
- a server device; and
- a portable electronic device, comprising:
  - one or more processors configured to:
    - detect a first image representing the clinical data by periodically monitoring image data to identify one or more features of the first image, wherein the first image is a quick response (QR) code, wherein an image capture device of the portable electronic device captures the first image responsive to detecting the one or more identified features of the first image;
    - present a user interface element to receive a selection of an identifier of the patient;
    - encrypt the identifier of the first patient and at least one of the first image or the clinical data;
  - the server device configured to:
    - decode a data structure to extract the clinical data;
    - update a patient data record corresponding to the patient in a clinical database maintained by the server device;
    - generate presentation data using the extracted clinical data; and
    - provide the presentation data to the portable electronic device for presentation by the portable electronic device.

19. The clinical communication system of claim 18, wherein the at least one of the sensor device or the treatment device comprises a portion of memory to store the clinical data, the portion of memory isolated from one or more applications that use a wireless communications circuit of the at least one of the sensor device or the treatment device.

\* \* \* \* \*